United States Patent [19]

Lash et al.

[11] Patent Number: 4,662,873

[45] Date of Patent: May 5, 1987

[54] INTRAVENOUS TUBE STRESS RELIEF BRACELET

[75] Inventors: Robert Lash; Gregory Hatfield, both of Foster City, Calif.

[73] Assignee: M.D. Engineering, Foster City, Calif.

[21] Appl. No.: 771,701

[22] Filed: Sep. 3, 1985

[51] Int. Cl.$^4$ ............................................. A61M 5/00
[52] U.S. Cl. .......................... 604/179; 128/DIG. 26; 224/219
[58] Field of Search ............................. 604/179, 180; 128/DIG. 28; 24/16 R, 16 PB; 224/219, 249

[56] References Cited

U.S. PATENT DOCUMENTS

| | | | |
|---|---|---|---|
| 2,361,506 | 10/1949 | Smith | 24/16 PB |
| 2,449,882 | 9/1948 | Daniels | 128/DIG. 26 X |
| 2,728,501 | 12/1955 | Hill | 224/219 |
| 3,059,645 | 10/1962 | Hassbrouck et al. | 128/DIG. 26 X |
| 3,138,158 | 6/1964 | Gordon et al. | 128/DIG. 26 X |
| 3,917,135 | 11/1975 | Christensen | 224/249 X |

*Primary Examiner*—Stephen C. Pellegrino
*Attorney, Agent, or Firm*—Harris Zimmerman; Howard Cohen

[57] ABSTRACT

A bracelet adapted to secure an intravenous tube to the wrist of a medical patient is formed of a single elongated strip of flexible plastic material. One end of the strip tapers to a rounded point, with a plurality of ratchet teeth formed in the edges of the strip adjacent to the tapered portion. The opposite end is provided with an opening to receive the first end and to engage the ratchet teeth and form a loop of adjustable length, with a pair of lateral slots provided to retain the distal portion of the first end flush with the bracelet. The medial portion of the strip includes a plurality of pairs of longitudinally extending slots, each pair adapted to receive the intravenous tube therethrough, so that the tube may be secured by describing a retrocurved configuration through the bracelet slots.

5 Claims, 6 Drawing Figures

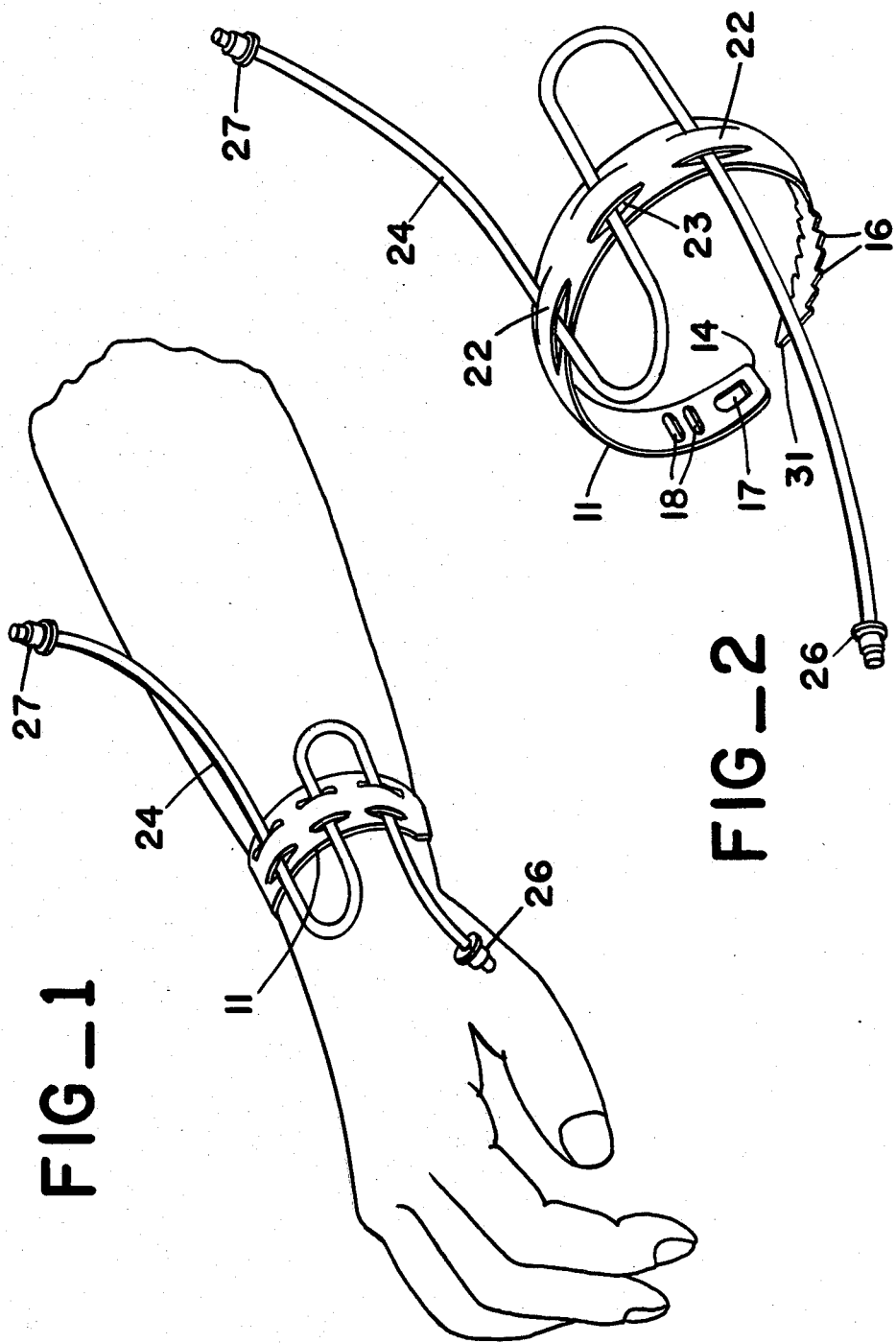

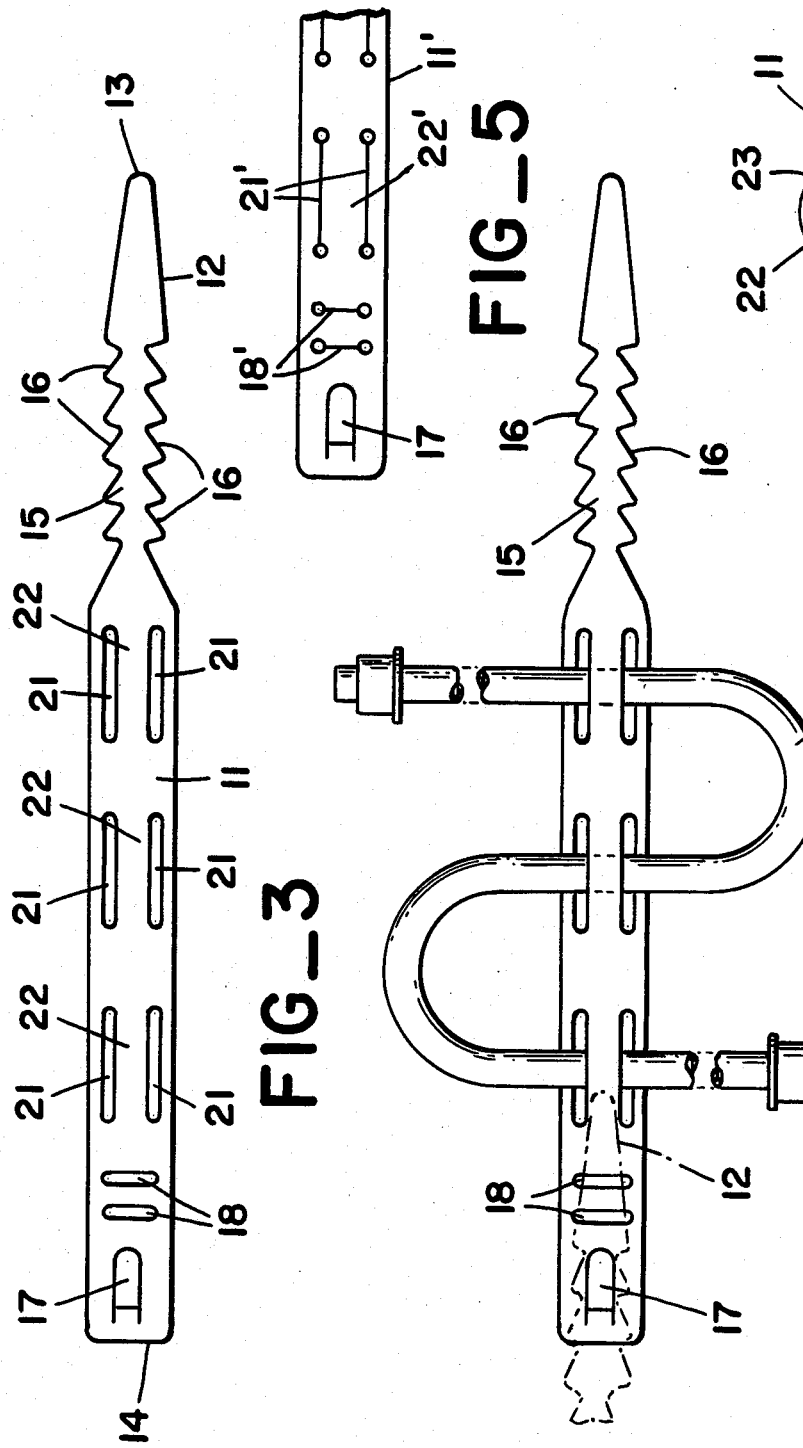

INTRAVENOUS TUBE STRESS RELIEF BRACELET

BACKGROUND OF THE INVENTION

In a wide variety of medical treatment situations, it is prudent and/or necessary to employ an intravenous catheter for the proper administration of fluids, medication, electrolytes, and the like. The most convenient location for the placement of the catheter is a vein in the hand or arm, due to the fact that the veins in this area are large, close to the skin, and easily located. After the intravenous needle is inserted in the vein and connected to the catheter tube, the tube is typically taped to the arm or hand to secure the tube and prevent accidental removal of the needle from the vein.

In many instances the tape applied to the tube is ineffective in protecting the catheter installation. Many patients inadvertently move in a manner which applies tension to the tube and pulls the needle from the insertion site. At times other individuals nearby may accidentally snag the tube and cause tension on it. At the least this can be painful to the patient; at the worst, the needle can be removed, causing interruption of the administration of the intravenous fluid. Clearly, serious medical consequences may result.

Also, many hospital patients are encouraged to walk and gain some exercise, even while an intravenous catheter is in place, by having the patient carry the intravenous fluid supply container while walking. This practice further increases the opportunity for the tube to become caught by nearby objects, resulting in accidental removal of the catheter. When the catheter is removed inadvertently, it is frequently the case that the vein insertion point is lacerated slightly, requiring that a new insertion point be used. The number of convenient vien locations which are suitable for catheter insertion is limited, and trauma to these locations may be injurious to the health of a frail patient.

There are known in the prior art several devices for securing the intravenous catheter tube to the patient. In general, these devices have proved to be complicated to use, and not always effective in preventing inadvertent catheter removal. Furthermore, the prior art devices often involve combinations or fasteners and tube mounting members which are difficult to manufacture and therefore unduly expensive.

SUMMARY OF THE PRESENT INVENTION

The present invention generally comprises a device for retaining an intravenous catheter installation on the arm or hand of a medical patient. A salient feature of the invention is that it is extremely simple to manufacture and to use, yet it is extremely effective in relieving all strain from the catheter needle installation.

The present invention, comprising a bracelet adapted to secure an intravenous tube to the wrist of a medical patient, is formed of a single elongated strip of flexible plastic material. One end of the strip tapers to a rounded point, with a plurality of ratchet teeth formed in the edges of the strip adjacent to the tapered portion. The opposite end is provided with an opening to receive the first end and to engage the ratchet teeth and form a loop of adjustable length, with a pair of lateral slots provided to retain the distal portion of the first end flush with the bracelet.

The medial portion of the strip includes a plurality of pairs of longitudinally extending slots, each pair disposed in parallel, adjacent relationship to define a web therebetween. Each web may be expanded from the nominal plane of the bracelet strip to form an opening therebetween adapted to receive the intravenous tube therethrough. The intravenous catheter tube may be passed through adjacent openings in a retrocurved configuration, thereby isolating the catheter needle portion from tensile stress applied inadvertently to the catheter tube joined thereto.

BRIEF DESCRIPTION OF THE DRAWING

FIG. 1 is a perspective view of the intravenous tube stress relief bracelet of the present invention, shown secured to the wrist of a medical patient.

FIG. 2 is a perspective view of the bracelet as depicted in FIG. 1.

FIG. 3 is a plan view of the strip which forms the intravenous stress relief bracelet of the present invention.

FIG. 4 is a partial side elevation of the bracelet-intravenous tube support of the present invention.

FIG. 5 is a partial plan view of a further embodiment of the strip which forms the bracelet of the present invention.

FIG. 6 is a plan view of the bracelet of the present invention, shown with the intravenous tube extending through the openings therein.

DESCRIPTION OF THE PREFERRED EMBODIMENT

The present invention generally comprises a device for securing an intravenous catheter tube to the wrist or arm of a patient. With regard to FIG. 3, the device is formed as a long, narrow, planar strip 11 of flexible material, such as one of the many flexible, plastic polymer compounds known in the prior art. The distal end portion 12 of the strip 11 is tapered toward a rounded point 13, and the opposite, proximal end 14 is provided with a generally rectangular end configuration.

Adjacent to the tapered portion 12, the strip is provided with a portion 15 having a plurality of ratchet-like teeth 16 formed in the opposed side edges of the strip. The two rows of teeth 16 are in parallel registration, so that each pair of opposed teeth together form a section of the strip which flares outwardly toward the proximal end and terminates in a root portion extending inwardly toward the midline of the strip of an angle approaching 90°. The flared sections are disposed serially along the portion 15 of the strip. It may be noted that the maximum width of the flared sections is substantially the same, and is equal to the maximum width of the strip portion 12. This maximum width is generally less than the width of the major portion of the strip 11.

Adjacent to the proximal end 14, the strip 11 is provided with a detent slot 17 adapted to receive the distal end portion 12 therethrough. Indeed, the width of the slot 17 is approximately equal to the root width dimension of the ratchet-toothed portion 15, and the diagonal dimension of the slot 17 is substantially equal to the maximum width of the strip portion 15. The tapered portion 12 may be inserted in the opening 17, and pulled through, causing the wider part of the portion 12 to deform as it passes through the somewhat narrower opening 17. When the first narrow section of the portion 15 passes through the opening 17, as shown in phantom line in FIG. 6, the strip is retained in a loop configuration by the engagement of the ratchet edges in the opening 17. It may be appreciated that the end 12 may be pulled further through the opening 17 to decrease the circumference of the bracelet loop thus formed, so that the bracelet may be adjusted to fit wrists or arms of various diameters and circumferences. The strip is also provided with a pair of slots 18 disposed adjacent to the opening 17 and extending transversely to the midline of the strip. The slots 18 are adapted to receive the excess portion of the distal end which is pulled through the opening 17 to adjust the size of the bracelet, so that the distal end excess is retained flush with the bracelet strip, as shown in FIG. 6.

A salient feature of the present invention is the provision of a plurality of paired slots 21 formed in the medical portion of the strip 11 and extending longitudinally therein. Each pair of slots 21 are disposed in adjacent, parallel relationship to define therebetween a medical web portion 22 therebetween. Each web portion 22 may be deformed outwardly from the nominal plane of the strip 11, thereby defining an opening 23 extending laterally through the strip between each web portion 22 and the corresponding laterally adjacent portions of the strip, as shown in FIG. 4. The lengths of the slots 21 are sufficient to define openings 23 which are adapted to receive therethrough a typical intravenous catheter supply tube 24.

The plurality of pairs of slots 21 are provided to define a like plurality of openings 23; in the preferred embodiment three openings 23 are provided. With the strip 11 disposed in a relatively flat, planar configuration, the intravenous supply tube 24 is passed through one opening 23, then bent to pass through the adjacent opening 23, and then retrocurved to pass through the remaining opening 23. Thus the tube defines a general "S" curve configuration. The strip is then placed about the wrist or arm of the patient, and secured in a closed loop as described previously and shown in FIG. 1. One end 26 of the tube is then connected to the catheter needle (not shown), which is subsequently placed in the vein of the hand or the like. The other end 27 is then connected to the intravenous fluid supply bottle or container, as is known in the prior art.

A significant feature of the invention is that the deformation of the strip 11 from the relatively planar configuration (FIG. 6) to the loop configuration of the bracelet (FIGS. 1 and 2) causes the web portions 22 to impinge with greater frictional effect on the tube 24 extending through the openings 23. As a result, the tube 24, which may easily be translated through the openings 23 when the strip is in the planar configuration, becomes clamped in place when the bracelet loop is formed. Consequently, the tube 24 cannot be pulled through the bracelet, and any tension applied inadvertently to the tube 24 cannot be transferred through the "S" configuration of the tube to the end 26 thereof. Therefore, virtually all tensile stress on the tube is isolated from the needle end 26, and the possibility of the catheter needle being accidentally dislodged is substantially eliminated.

It may be appreciated that the stress relief bracelet of the present invention is extremely simple in form and manufacture, yet is extremely effective in securing an intravenous catheter tube and in preventing removal thereof. Indeed, the strip 11 may be die cut in a one pass operation, resulting in very low manufacturing costs. In a further embodiment of the invention, shown in FIG. 5, the strip 11 includes the same detent opening 17 as previously described. However the slots 18 and 21 are replaced by slit openings 18' and 21', each having stress relief terminations at every end thereof, as is known in the prior art. The slits 18' and 21' function substantially the same as the correspondingly numbered components described previously, and may be die cut with equal ease.

We claim:

1. A device for securing a tube to the limb of a person, including; a generally flat, elongated strip of flexible material having opposed ends, said strip being adapted to be deformed into a bracelet loop configuration, means for joining said opposed ends in a bracelet loop of selectively variable length, a plurality of pairs of slot openings disposed in a medial portion of said strip and extending generally longitudinally therein, each pair of said slot openings defining therebetween a medial web portion, each of said medial web portions being deformable from the nominal plane of said strip to define one of a trio of first openings in said strip, the tube describing an "S" configuration through said first openings, and means in said first openings for frictionally clamping a tube therein when said strip is deformed into said bracelet loop configuration.

2. The device of claim 1, further including a tapered end portion at said one end of said strip.

3. The device of claim 2, further including a pair of laterally extending slots disposed adjacent to said detent opening and adapted to receive and secure said tapered end portion of said one end.

4. The device of claim 1, wherein each of said medical web portions is adapted to apply frictional clamping pressure to the tube portion passing thereby when said strip is configured in said bracelet loop.

5. A device for securing a tube to the limb of a person, including; a generally flat, elongated strip of flexible material having opposed ends, said strip being adapted to be deformed into a bracelet loop configuration, means for joining said opposed ends in a bracelet loop of selectively variable length, a plurality of slits formed in said strip to define a plurality of medical web portions extending substantially longitudinally therein each of said medial web portions being deformable from said strip to define one of a plurality of first openings therein, said first openings being dimensioned to receive the tube therethrough in freely translating fashion when said strip is generally flat, said medial web portions frictionally clamping the tube when said strip is deformed into a curved, bracelet configuration.

* * * * *